(12) United States Patent
Chute et al.

(10) Patent No.: US 10,661,471 B2
(45) Date of Patent: May 26, 2020

(54) APPARATUS FOR SHIPBOARD HEAT TREATING

(71) Applicant: PHYTO-CHARTER, INC., South Casco, ME (US)

(72) Inventors: Stephean C. Chute, South Casco, ME (US); Larry Carrier, Wilton, ME (US)

(73) Assignee: PHYTO-CHARTER, INC., South Casco, ME (US)

( * ) Notice: Subject to any disclaimer, the term of this patent is extended or adjusted under 35 U.S.C. 154(b) by 737 days.

(21) Appl. No.: 15/022,481

(22) PCT Filed: Sep. 24, 2014

(86) PCT No.: PCT/US2014/057299
§ 371 (c)(1),
(2) Date: Mar. 16, 2016

(87) PCT Pub. No.: WO2015/048185
PCT Pub. Date: Apr. 2, 2015

(65) Prior Publication Data
US 2016/0229079 A1    Aug. 11, 2016

Related U.S. Application Data

(60) Provisional application No. 61/883,014, filed on Sep. 26, 2013.

(51) Int. Cl.
*B27K 5/00* (2006.01)
*A61L 2/04* (2006.01)
*A61L 2/06* (2006.01)

(52) U.S. Cl.
CPC ............... *B27K 5/001* (2013.01); *A61L 2/04* (2013.01); *A61L 2/06* (2013.01); *B27K 2240/20* (2013.01)

(58) Field of Classification Search
CPC ........ F26B 23/02; F26B 23/028; F26B 23/10; F26B 2200/24; F26B 2210/16; B27K 5/001; B27K 2240/20; A61L 2/06; A61L 2/04
See application file for complete search history.

(56) References Cited

U.S. PATENT DOCUMENTS 4,817,329 A    4/1989    Forbes
4,799,621 A    6/1989    Reith
(Continued)

OTHER PUBLICATIONS

Phytosanitary Risks Associated with the Global Movement of Forest Products: A Commodity-Based Approach by Leal et al. Canadian Forest Service Pacific Forestry Centre Information Report BC-X-419: 2010, Retrieved from the Internet Nov. 10, 2014 URL: http://www.cfs.nrcan.gc.ca/pubwarehouse/pdfs/32149.pdf—Entire document, especially p. 2, col. 2, para 2; p. 7, col. 2, para 2-4; p. 8, item 7.

(Continued)

*Primary Examiner* — Jessica Yuen
(74) *Attorney, Agent, or Firm* — Leber IP Law; David C. Robertson

(57) ABSTRACT

A shipboard apparatus (300) for heat treating wood chips, for service in the trade and for export to receivers within the forest products industries and the biomass energy sectors. The purpose of heat treating wood fiber is to provide certification to meet the phytosanitary requirements of wood fiber importing countries, infusion of moisture laden, saturated heated air using a closed loop system (301, 303a, 303b, 304a, 304b, 305, 310) within the holds of the ship with the heating apparatus being situated on the quay while the ship is being loaded with wood chips. The completed heat treating process renders the cargo acceptable for issuance of a phytosanitary certificate.

15 Claims, 5 Drawing Sheets

(56) References Cited

U.S. PATENT DOCUMENTS

| | | | | | |
|---|---|---|---|---|---|
| 5,578,274 | A | * | 11/1996 | Seidner | B27K 1/02 114/73 |
| 5,943,789 | A | * | 8/1999 | Yamamoto | F26B 3/00 34/217 |

OTHER PUBLICATIONS

Search Report—Corresponding PCT Application No. PCT/US14/57299, dated Dec. 4, 2014, 1 page.
"Exploring Developments in the Wood Chip Market", Argus Media Group, 2017, Slide No. 3, downloaded from www.argusmedia.com/eurobiomass on Mar. 20, 2019, 9 pages.
"Argus Biomass 2019 Industry Survey Results", Argus Media Group, 2018, downloaded from www.argusmedia.com/eurobiomass on Mar. 20, 2019, 12 pages.

* cited by examiner

APPARATUS FOR SHIPBOARD HEAT TREATING

RELATED APPLICATIONS

The present application claims priority from U.S. Provisional Patent Application No. 61/883,014 filed 26 Sep. 2013, the contents of which are herein incorporated by reference.

FIELD OF THE INVENTION

The present invention relates to heat treating systems. In particular, although not exclusively, for heat treatment of wood fiber or agricultural products within the hold of a cargo vessel.

BACKGROUND OF THE INVENTION

World production of wood and wood products has increasingly relied upon international trade and the demand for imported wood and wood products can only be expected to increase throughout the world. Moreover, potential supplies for additional wood and wood products are located in remote places such as Russia, New Zealand, Chile and Brazil. An obstacle to importation of green wood and wood products from such varied locations is the danger that foreign products could introduce and spread exotic plant pests throughout the jurisdiction where the products are imported.

Likewise, some jurisdictions like the United States have become large exporters of wood and wood products. However, there are also a number of plant pathogens native to the United States, including the pine wilt nematode (*Bursaphelenchus xylophilis*) occasionally found in the several species of pine and which are not found in overseas forests. The incursion of this pathogen has caused devastation of natural conifer forests in Portugal and have been reported in certain Scandinavian countries. These pathogens create an obstacle to exporting North American wood fiber to overseas markets in a broader context than the several species of pine, whereas the industry practice of aggregating species and cargos. It is therefore necessary to prophylactically heat treat all wood-fiber passing into world trade.

There are several well understood methods for destroying plant pathogens. Unfortunately, each suffer from drawbacks, especially when considered in the context of treating wood and wood products to be transported overseas. For example, it is well settled that heat-treating wood and wood products, typically in a kiln with an attendant reduction in the moisture content of the material, is an effective method for killing plant pathogens. Such heat-treatment processes require bringing the core of the material to a certain minimum temperature for a certain minimum period of time so as to dry the material without causing any cellular or structural degradation.

Even when wood and wood products are heat treated by kiln or dryer, there remains a risk of reinfestation by plant pathogens. Unless the wood and wood products' environment is carefully monitored and controlled, reinfestation can occur before the materials are loaded aboard a cargo vessel for transportation. Even after they are loaded, cross contamination may occur if the vessel contains infested cargo that has not been treated.

One approach to the problem is fumigating wood and wood products once a ship carrying a load of wood or wood products in transit or has completed its journey. This is a customary practice of eliminating pathogens in both the United States and other countries, such as Japan. Fumigation effectively controls plant pathogens that may be associated with the surface and subsurface of debarked logs and other wood products. Fumigation may not be effective in killing other plant pathogens that bore deep into the wood or in killing microscopic organisms that live in the wood's cells. Disadvantages of fumigation include the expense of the fumigant. Another significant drawback of fumigation is that it has been known to pose a health risk to people and the environment. Typical fumigants often include methyl bromide fumigation which can only be carried out under carefully controlled circumstances, usually once the ship has entered port and the crew has been safely removed. This further adds to the environmental risk, time and expense involved in importing wood and wood products which are treated in this manner.

Another obstacle to importing green wood and wood products, especially logs, lumber, wood chips or wood strands from across the seas is the condition of the wood or wood product when it arrives at its destination. A freshly cut log has moisture content of about 50%. As a general rule, because of the evaporation of surface and internal moisture, the longer the period of time since the tree has been cut, the drier the wood becomes. The increasing dryness of a log is a drawback in such subsequent manufacturing processes as the manufacture of lumber or veneer. If care is not taken during the period after felling the tree and continuing up through its shipping, moisture variations cause degrees of wood degradation such as cracks and checks. Moreover, incipient rot can form. These phenomena all make portions of the wood unusable in or less valuable for subsequent fabrication, such as fabrication into lumber or veneer or oriented strand board. Similarly, if care is not taken with wood chips or wood strands, there can be a significant loss of fiber, which can destroy or greatly reduce the value of the wood.

European Union Standing Committee on Plant Health, Council Directive 2000/29/EC of 8 May 2000 is one government mandate related to protective measures against the introduction of organisms harmful to plants or plant products and against their spread within Europe. In terms of wood products, this mandate may be met by land based heat treating systems. These systems are essentially wood chip drying plants, long used in board mills, and pellet mills for preparing the wood fiber for further processing.

Standard drying systems are not suitable for the export requirements of wood fiber and represent impediments in several respects. The capital requirements of an engineer, procure and construct (EPC) program for a heat treating plant have deterred private sector industry from constructing a wood chip heat treating plant proximate to a shipping port. Conventional wood chip drying plants would be of such a large scale to meet the compressed time restrictions under USDA phytosanitary requirements to be logistically inefficient. The present drying plant technology customarily reduces the moisture content of woodchips to below 20% which is an inefficient use of the energy medium and is not necessary to phytosanitary requirements.

Drying mechanisms and structures as current technology applies to shipping, dries the wood fiber in batches or continuous process and concentrates the treated wood chips on a chip pad at a shipping port in advance of loading. The volume constraints of the drying systems require long lead times from drying the fiber and readying the cargo for shipment. As previously mentioned, these systems expose the wood fiber to the risk of being re-infested with prohibited microbes from wood processing operations in communication with the treated cargo.

Accordingly, there has existed a definite need for safe, effective and inexpensive apparatus for eliminating significant plant pathogens risks from green wood and wood products, including large volumes of green logs, sawn lumber, wood chips and wood strands transported overseas. There has also existed a need for a method which minimizes the risk of reinfestation of plant pathogens after the initial treatment. There has existed a still further need for a method for maintaining the fresh-cut characteristics of wood and wood products delivered from overseas by reducing the incidence of cracks, checks and incipient rot or, in the case of wood chips or wood strands, by minimizing fiber loss. It would be advantageous to obviate or mitigate these disadvantages.

SUMMARY OF THE INVENTION

In general, the present invention presents an apparatus for shipboard heat treating of wood and wood products in order to obviate or mitigate the above stated disadvantages of the prior art and provides further related advantages. Moreover, the present invention avoids the possibility of post-treatment contamination by carrying out the heat treatment after the cargo has been stowed and quarantined within the vessel. In an illustrative implementation, the present invention is embodied in a saturated heated air infusion apparatus deployed within the hold of a specialized wood chip carrier.

According to one aspect of the invention there is provided an apparatus for shipboard heat treating of green wood chips, the apparatus including: a heating device; ductwork operably connected to the heating device; and conduit for placement within a hold of a cargo vessel, the conduit connected to the ductwork; wherein the heating device provides heated air which saturates with moisture in the presence of green wood chips within the hold by way of the conduit.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
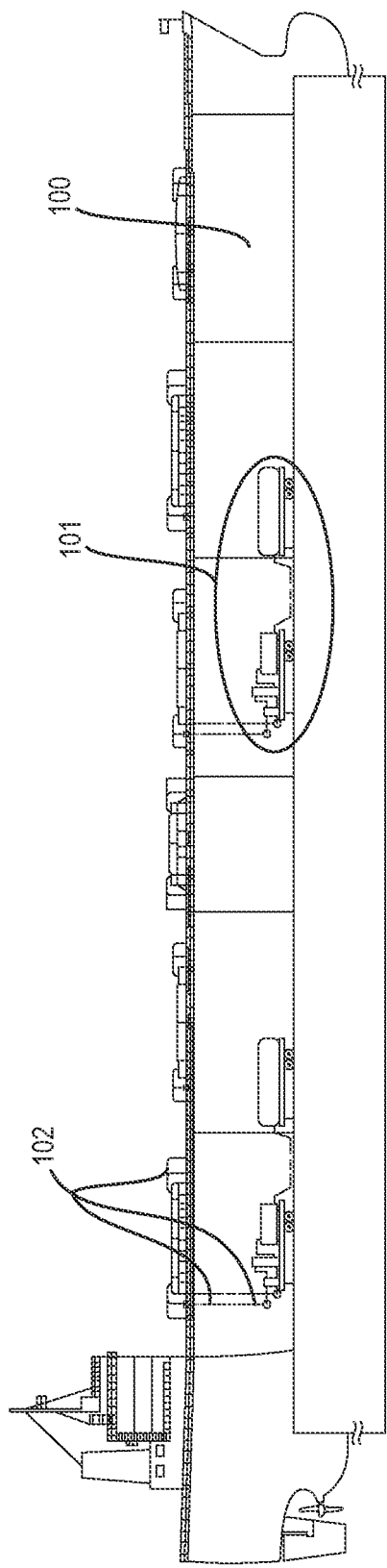
FIGS. 1 and 2 are side and top views of a cargo vessel including the present invention and showing one possible general configuration of a plurality of heat treatment chambers therein.
Figure 2:
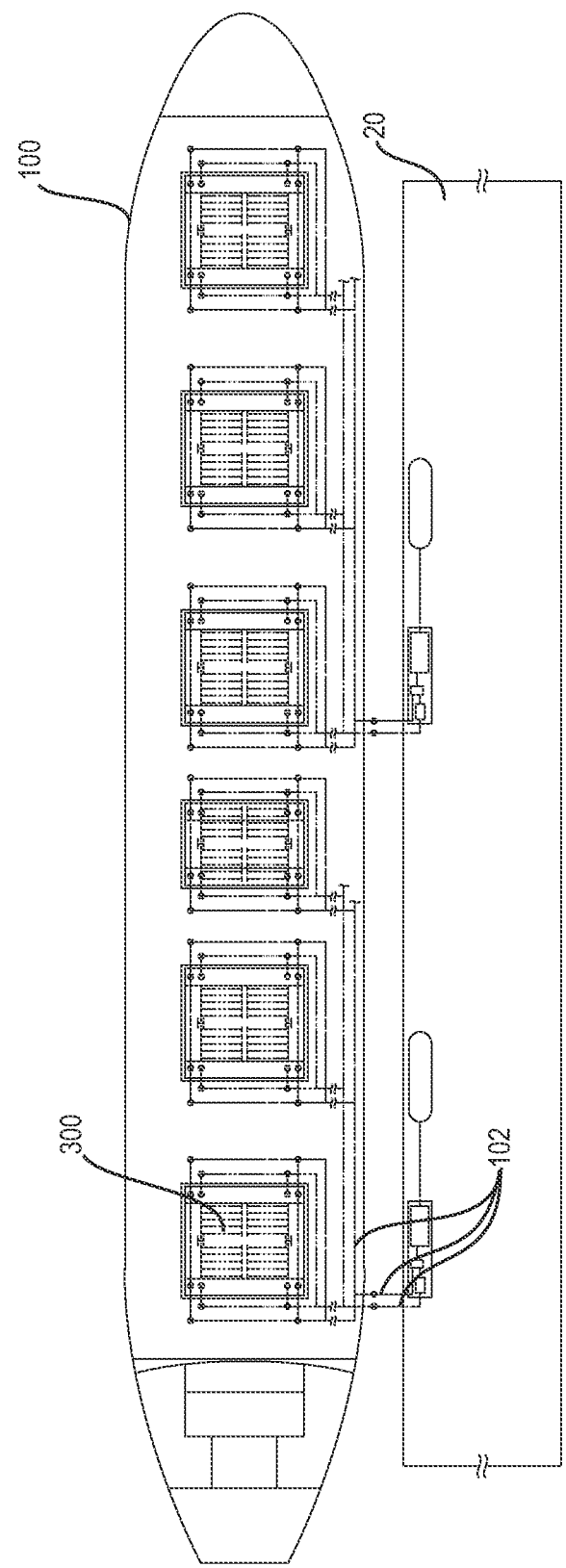

In accordance with the present invention and as shown in FIGS. 1 and 2, the heat treating process occurs during loading of the cargo of wood chips within holds of a vessel 100 (i.e., wood chip cargo vessel). It should be understood that the term "wood chips" will be construed to include in-woods chipping, residual wood chips, wood grindings, and the like. Heating apparatus 101 includes a variety of heating devices including gas furnaces, heat exchangers and blowers and a fuel source such, but not limited to, propane tanks. Such heating apparatus 101 is typically stationed upon the quay apron 20 while the vessel 100 is moored to the pier bollards. The heat treating apparatus 300 is provided within several discrete chambers or holds within the carrier 100 (six chambers shown with six corresponding heat treating apparatuses, though this numbers may vary based upon the overall size of the given vessel without straying from the intended scope of the present invention). Flexible insulated ductwork 102 (i.e., flexduct) is extended from the heating apparatus 101 on the quay up and over the deck of the vessel and connected to the holds through "hatch panel" penetrations.

In implementing the present invention, the heating apparatus 101 may alternatively (though not shown) be housed in sea container type units (e.g., intermodal ISO containers) that allows for portability of the apparatus which remains on the quay and connectable to a generator for power supply and to propane or compressed natural gas tanker trucks. For a standard cargo ship, the heating apparatus may be formed as two furnace modules per hold. Each furnace module may consist of a 7,200,000 BTU/h input gas furnace. All gas connections will be brought to a single point at the edge of the module for easy connection. In each module, there may be one 50,000 CFM blower capable of overcoming 50-60" static pressure within the chamber. The blower may be direct driven by a 600 HP blower motor controlled by a variable frequency drive. Each module will include a computer based control system and programmable logic controls (PLC) designed for safety and operational control of the heating apparatus. The air pressure is monitored to reduce blower energy consumption and prevent excessive pressure in the furnace modules.

It should further be noted that the heat source for the heating apparatus may be obtained from scavenged heat from the stack, propulsion, and/or electrical generating systems within the cargo vessel.

Figure 3:
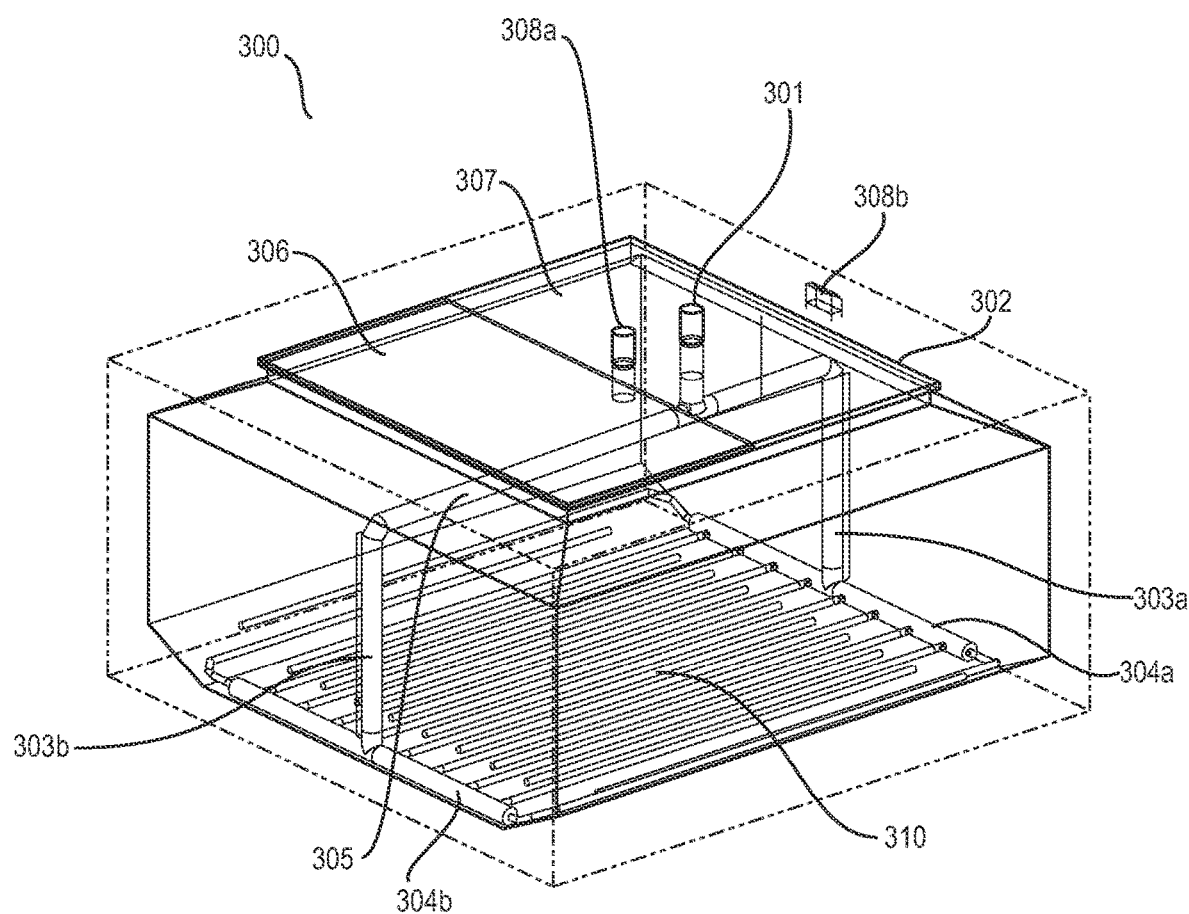
FIG. 3 is a perspective view of a single heat treatment chamber according to one embodiment of the present invention.

With reference to FIG. 3, the heat treating apparatus 300 is shown within a single chamber denoted by dotted lines for illustrative clarity within the hold of the given vessel. It should however be readily understood that each chamber and related heat treating apparatus therein are substantially identical to one another. Accordingly, for illustrative clarity only one chamber and corresponding heat treating apparatus 300 will be detailed. Each chamber will of course include a hatch 302 through which wood chips (not shown) are loaded via ship loading conveyor systems as is a convention within the industry. Loading occurs with the hatch in the open position. The procedure for unloading would be in reverse whereby wood chips may be offloaded by means of shipboard cranes operating orange peel grabs (i.e., electro-hydraulically operated grappling composed of an electric engine, pump and electro-hydraulic valves which provide the pressure to the system and grab's jaws), or the equivalent, as is a convention in the industry.

Once loaded and the hatch cover 306 is still open, a temporary hatch cover 307 is placed atop the opened half of the hatch 302. The chamber is outfitted (such installation discussed further herein below) with ductwork arranged so as to distribute fully moisture-laden, saturated heated air from the heating apparatus 101 on quay apron 20 to the load of chips situated (once loaded) within the chamber. The heated air enters the chamber through an input port 301 penetrating the temporary hatch panel 307 set in the coaming, while the hatch cover 306 is in the open position. It should therefore be understood that the hatch panels replace, temporarily, the hatch covers only while the heat treating is being carried out.

Once through the plane of the hatch 301, the input port 301 T-branches to ductwork 305 arranged along the upper surface of the chamber. This redistributes heated air towards the sides of the chamber to vertical ducts 303*a* and 303*b*. In turn, ducts 303*a* and 303*b* each laterally redistribute heated air to manifolds 304*a* and 304*b*. Each of the ductwork elements from input 303 through manifolds 304*a*, 304*b* are of course insulated so as to maintain the heat level of the air therein. Each chamber may include two air plenums 308*a*, 308*b*: one each for supply and for return to balance the air flow through the heating apparatus and the duct connections.

From each manifold 304*a*, 304*b*, a set of heat distribution pipes 310 are provided. While eight heat distribution pipes 310 are shown coming from each manifold, it should be understood that the number of pipes may vary in accordance with the dimension of the chamber. Each set of heat distribution pipes 310 are interleaved symmetrically to facilitate equal distribution from either manifold 304*a*, 304*b*. Such interleaving is more clearly shown in FIGS. 4 and 5 which, respectively, show perspective and top views of the manifolds and heat distribution pipes. From each end of the manifolds 304*a*, 304*b*, there are piping wings 311*a*, 311*b* which extend towards the lower outside chamber edges and vertically upwards. This configuration of the piping wings 311*a*, 311*b* accomplishes both further distribution of the heated air to the outermost (relative to the longitudinal axis of the vessel) side edges of the chip pile and also advantageously compensates for the ambient seawater temperatures which communicate with the corresponding starboard and port hull walls of the shipping vessel within which the chamber resides.

With reference to operation of the present invention and with regard to FIG. 3 as previously described above, it should therefore be readily apparent that the heated air is infused into the chamber by means of a closed loop system into each chamber. This is accomplished by means of high volume blowers (not shown) along with insulated duct work (301, 303*a*, 303*b*, 304*a*, 304*b*, 305) which connect to piping (310, 311*a*, 311*b*) arranged on the lower surface of each chamber as previously described.

During the heat treatment process, the hatch covers are in an open position and are replaced with the temporary hatch panels fitted with penetrations for duct ports which renders a substantially airtight chamber to thereby close the loop within the system. Heated air is forced up through the cargo of wood chips under slight pressure sufficient to overcome the static pressure of the stowed cargo. Moisture saturation of the heated air occurs via the water content within the "green" wood chips distributing water into the heated air and this saturation is held via recirculation. Spent saturated air is pulled off via the regulated vent 303 from the top of the stowed holds by a means of insulated duct work (not shown) and a slight vacuum, returning the saturated air through the heat exchangers located on the quay apron as previously mentioned. The process of recirculating saturated heated air continues until the entire chamber is heated to 60° C. for a period exceeding 30 minutes.

By means of recirculating moisture laden air that is heated to 60° C., the wood chips with a natural state moisture content averaging 48% are fully heated through to the core. It is desirable to keep the air infused within the hold as close to 60° C. as possible whereas higher temperature would result in overheated cargo and energy inefficiency. The air temperature will be approximately 60° C. maximum and the air pressure in the hold will be monitored to be at atmospheric pressure at the return ducts. The system will run until the return air temperature is 60° C. after passing through the woodchip cargo. The system then shuts down, the hold is reopened and the same procedure is repeated for each trim until the hold is fully stowed.

The apparatus in accordance with the invention may include hard wired or wireless thermocouple sensors deployed at the hatch coamings as a means of collecting heating process data under an operational and control protocol. The sensors may be deployed symmetrically interleaved at additional locations throughout the chamber and are in communication with the computer based control system and PLC to ensure for safe operation and control of the heating apparatus and related heated air movement. Data readings from the sensors will determine the length of heat cycles and may provide a computer output in the form of an electronic report providing the basis for certifying that the expended heated air from the holds exceed the requisite temperature threshold—e.g., 60° C. The electronic report may be stored and/or simultaneously electronically transmitted in real time as generated. Thus, the inventive apparatus of heat treating and resultant computer output provides an electronic record transmittable in real time to the operators and agents of the United States Department of Agriculture, Animal and Plant Health Inspection Service (U.S.D.A. (APHIS)) for phytosanitary export certificate.

The computer based control system and PLC may include sensors to measure performance of various components and to measure temperatures in accordance with applicable codes. The blower speed will be automatically controlled based on return air pressure. The computer based control system and PLC may include a user interface with color screen that will display all collected data. The computer based control system and PLC may allow each module to connect directly to a computer control that is within 1500 feet of the furnace module and will store data and allow connection to the Internet or to a central computer at the site.

Figure 4:
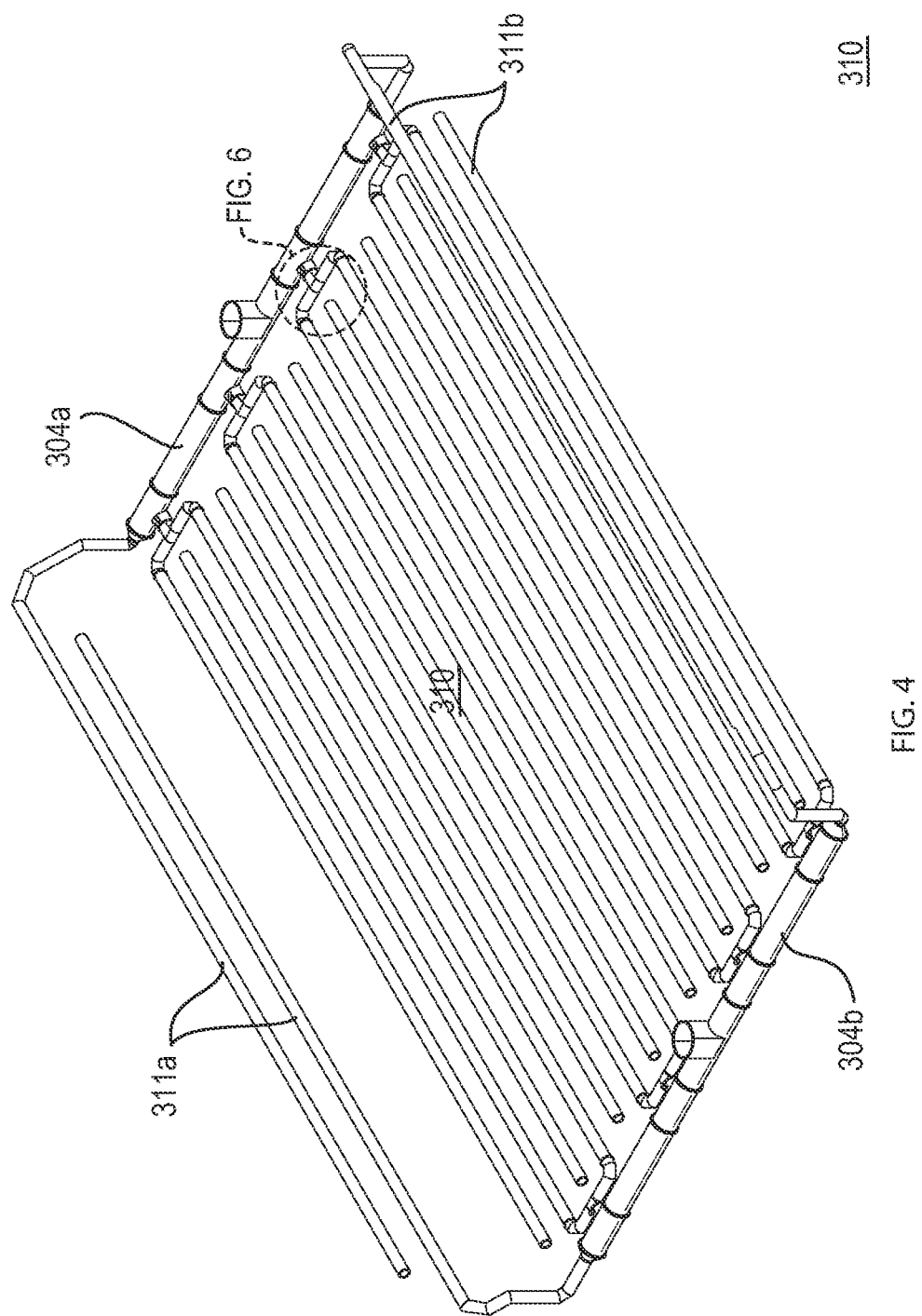
FIG. 4 is an illustration of the heat conduits of the single heat treatment chamber of FIG. 3.
Figure 5:
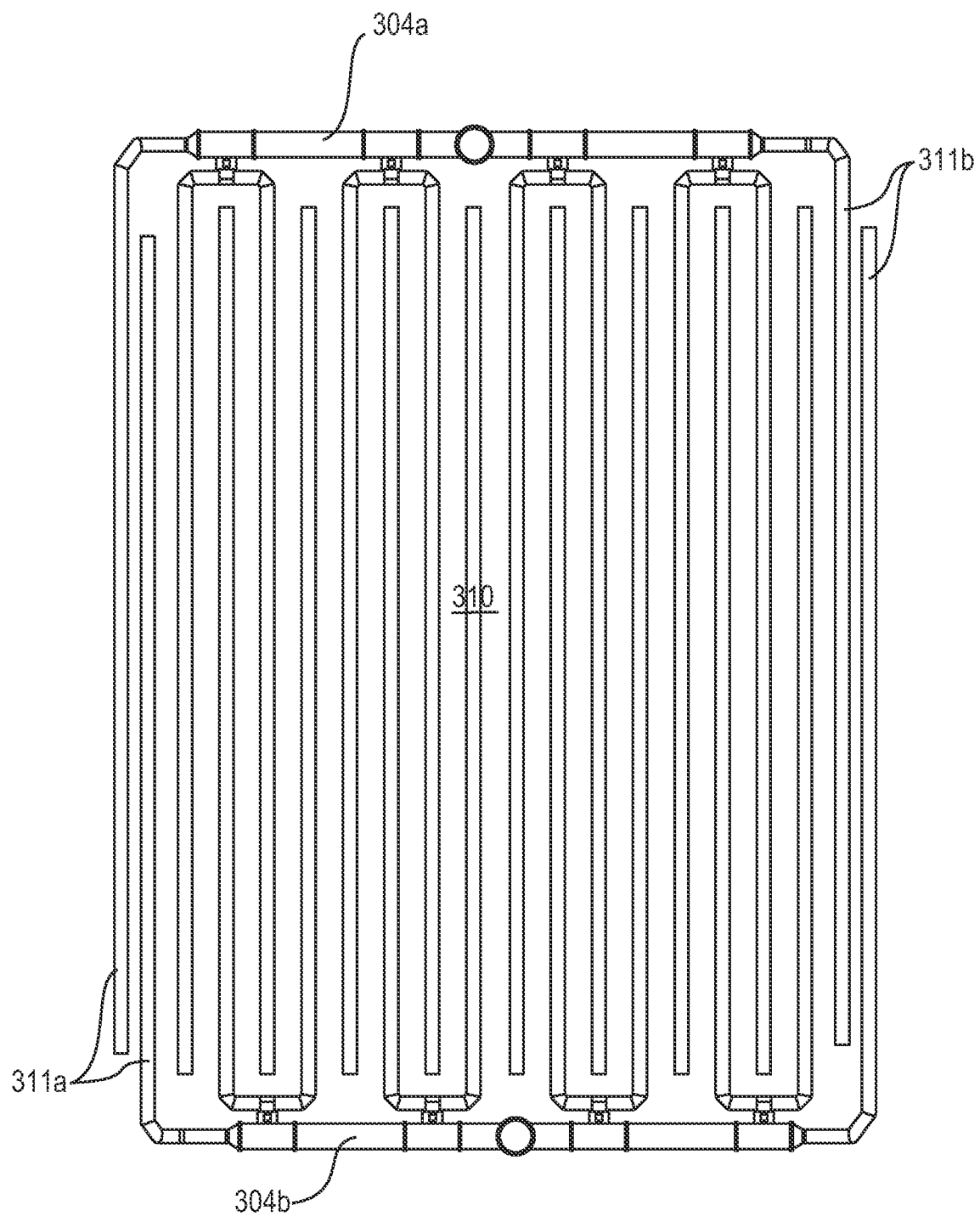
FIG. 5 is a top view corresponding to the illustration as shown in FIG. 4.
Figure 6:
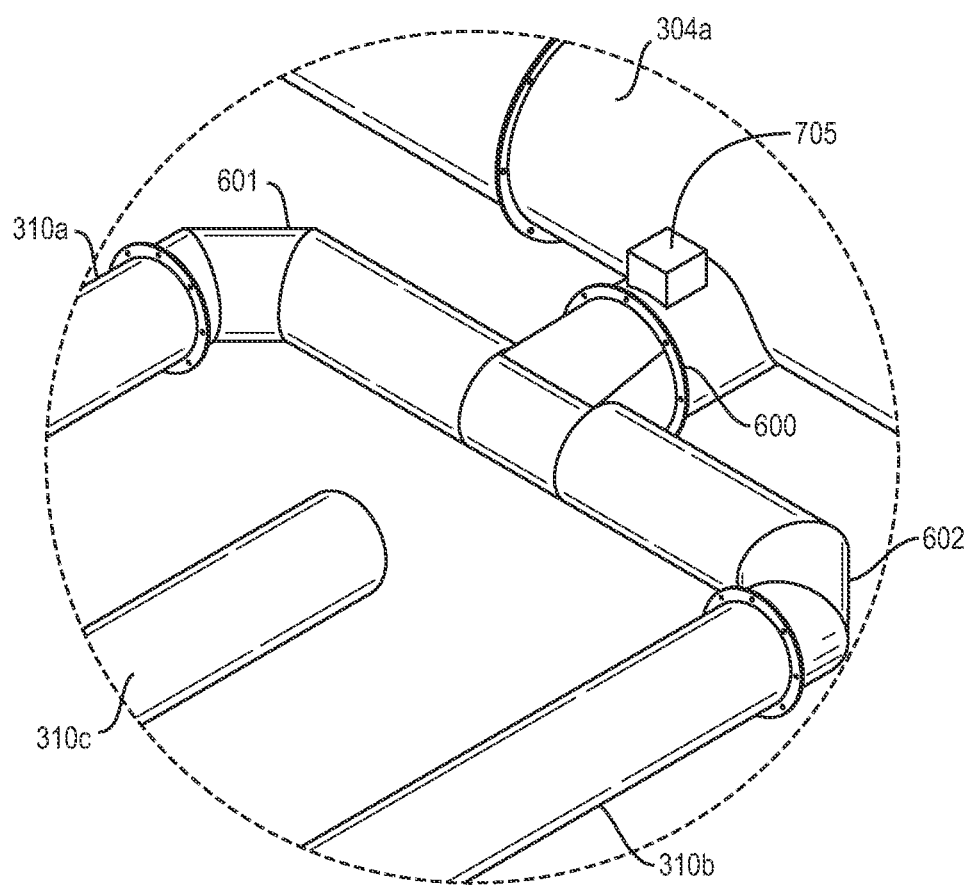
FIG. 6 is a close up view corresponding the dotted line circle detail denoted in FIG. 4.
Figure 7:
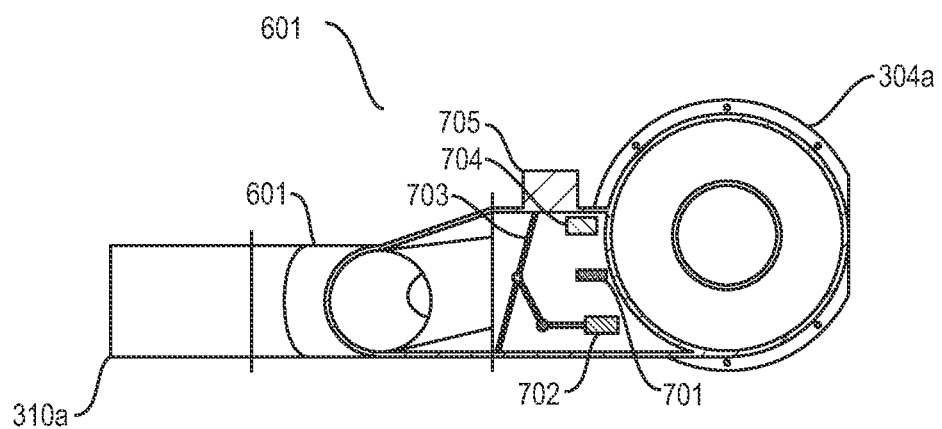
FIG. 7 is a cutaway side view taken along the center of FIG. 6.

With reference to FIG. 6 there is shown a close-up perspective view corresponding to the dotted line detail are in FIG. 4 including a T-branch supply header 600. Likewise, FIG. 7 is a cutaway view of one such T-header showing the inner elements. These views illustrate the junction of the manifold 304*a* to the distribution pipes 310*a* and 310*c*. Pipe 310*c* is shown though that pipe is connected to the opposite manifold 304*b*. While pipes 601 and 602 may be formed from flexible, non-perforated conduit, it should be readily apparent that pipes 310*a*, 310*b*, and 310*c* are formed from perforated conduit. Here, the infused air from the supply header 600 is controlled by a damper 703 actuated via pneumatic piston 702. Air velocity sensor 701 and temperature sensor 704 provide feedback data via control electronics 704 which operate in conjunction with the PLC devices (previously mentioned herein above) which control the dampers 703 so as to adjust the air velocity and temperature. The resultant controlling of the air infusion ensures the efficient distribution of heat throughout the chamber.

The present invention is particularly suited to the export trade by wood chip receivers in the market pulp industry, as well as board mills, including medium density fiberboard, (MDF), oriented strand board (OSB), and the biomass energy sector, including power plants, wood pellet mills and wood Torre faction plants. Other applications may include heat treating of agricultural products where fumigation is not preferred or permitted.

Although the present invention is shown in FIGS. 1 and 2 in situ within a cargo vessel, it should be readily apparent that the invention may be applied after the fact to any suitably dimensioned cargo hold within a vessel. In order to prepare a vessel's cargo hold for receipt of wood chips within the context of the present invention, the hot air infusion piping will be arranged by stevedores on what is typically referred to as the tank tops within the given vessel's holds. The hot air infusion piping will then be connected to the manifolds which will in turn be connected to standpipes running vertically from the manifolds through penetration collars within the temporary hatch panels and fitted to the flexible, and insulated, duct works laid over the ship rails and dropped to the modular heat treating apparatus deployed on the quay. After the entire cargo has been heat treated, the duct work connected to each hold will be removed by stevedores and returned to the quay. The cargo holds will be allowed to naturally aspirate during transit. The flexducts arrayed out on the tank tops within the hold will be removed after discharge of the cargo. In this manner, virtually any suitably dimensioned cargo hold can become a heat treatment chamber in accordance with the present invention.

It should be readily apparent that the inventive apparatus will heat treat the cargo of wood chips within the holds of the chip vessel upon a sequence as determined by the loading schedule. The present invention may be deployed within multiple holds that correspond to the loading sequence prescribed by the ship's master and will be engaged after deploying the hatch panels between each cargo trim and then commencing the heating process.

Implementing the present invention provides a balance of positive pressure at the tank tops (i.e., lower portion of the chamber), moving to a negative pressure at the coamings (i.e., upper portion of the chamber), with the vacuum pulled off by the recirculating saturated air system. Equilibrium within the chamber is reached where the vacuum overcomes the static pressure of the chip cargo.

The loading sequence which specifies the order of holds and the tonnage stowed is determined by the master and mate of the vessel to control trim and ballast while moored at the pier bollards. The heat treating process will correspond with the loading sequence. As one hold is stowed and trimmed, the heat treating process will be commenced by positioning the temporary hatch panels with the hatch covers in the open position and commencing the circulation of saturated air through each trim of the specified hold. Loading of wood chips will be made at the nominal rate of 1000 gross metric ton per hour, accounting for repositioning ship loading gear and commencing heat treating and trimming the cargo. The process will conclude within the same lay time under the charter party for the allotted time for loading the chip vessel.

It should be further noted that the advantages and benefits of the present invention may be further enhanced by providing the saturated, heated air in the chamber with certain wood-treating ingredients which will penetrate the wood fiber. Such ingredients may include nematocides, fungicides, wood preservatives, or fire retardants.

Advantageously, the present invention provides a means of heat treating approximately 40,000 gross metric ton of wood chips at a time without incurring the inefficiencies of multiple handlings, while completing the process with the compressed time requirements of U.S.D.A. (APHIS) for issuance of a phytosanitary export certificate.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. An apparatus for shipboard heat treating of green wood chips, said apparatus comprising:
   a heating device;
   ductwork operably connected to said heating device; and
   conduit for placement within a hold of a cargo vessel, said conduit connected to said ductwork;
   wherein said heating device provides heated air which saturates with moisture in the presence of green wood chips within said hold by way of said conduit, said heated air heat transfer raising a core temperature of the green wood chips; and
   wherein said ductwork penetrates through temporary hatch panels of said cargo vessel and said conduit within said hold includes two manifolds arranged opposite one another with piping there between.

2. The apparatus as claimed in claim 1 wherein said heated air heat transfer to said green wood chips raises the core temperature of said green wood chips in excess of 56° Celsius for a period exceeding 30 minutes.

3. The apparatus as claimed in claim 1 wherein said piping is interleaved and connected in an alternating pattern to each of said two manifolds.

4. The apparatus as claimed in claim 3 wherein said piping includes a first set of pipes located along a bottom portion of said hold, a second set of pipes located adjacent a port side of said hold, and a third set of pipes located adjacent a starboard side of said hold, where said second set and said third set are vertically displaced from said first set.

5. The apparatus as claimed in claim 4 wherein said first set of pipes located along a bottom portion of said hold, a second set of pipes located adjacent a port side of said hold, and a third set of pipes located adjacent a starboard side of said hold, where said second set and said third set are vertically displaced from said first set.

6. The apparatus as claimed in claim 5 wherein spent saturated heated air is returned by way of vacuum within an upper portion of said hold.

7. The apparatus as claimed in claim 6 wherein said heating device provides heat scavenged from one or more systems within said cargo vessel.

8. The apparatus as claimed in claim 6 wherein said heating device is deployed adjacent said cargo vessel.

9. The apparatus as claimed in claim 6 wherein said heating device is deployed as a modular system.

10. The apparatus as claimed in claim 6 wherein said heating device is deployed on chassis.

11. The apparatus as claimed in claim 6 wherein said heating device is deployed is further comprised of one or more heat exchangers.

12. The apparatus as claimed in claim 6 further including at least one high pressure blower capable of producing an operating pressure sufficient to overcome static pressure of said hold with said green wood chips stowed.

13. The apparatus as claimed in claim 6 further including one or more programmable logic controllers and one or more thermocouples providing feedback to said one or more programmable logic controllers so as to maintain a constant supply of heated, moisture laden air to said green wood chips via said conduit.

14. The apparatus as claimed in claim 13 further including electronic recording devices of temperature within said hold.

15. The apparatus as claimed in claim 14 wherein said electronic recording devices provide real-time transmission of said temperature.

\* \* \* \* \*